US009709255B2

(12) United States Patent
Chen

(10) Patent No.: US 9,709,255 B2
(45) Date of Patent: Jul. 18, 2017

(54) SMART HOME-CARE SECURITY DEVICE

(71) Applicant: Kaipo Chen, Taoyuan (TW)

(72) Inventor: Kaipo Chen, Taoyuan (TW)

( * ) Notice: Subject to any disclaimer, the term of this patent is extended or adjusted under 35 U.S.C. 154(b) by 0 days.

(21) Appl. No.: 15/394,759

(22) Filed: Dec. 29, 2016

(65) Prior Publication Data
US 2017/0111561 A1  Apr. 20, 2017

Related U.S. Application Data

(63) Continuation-in-part of application No. 14/258,029, filed on Apr. 22, 2014, and a continuation-in-part of application No. 15/011,646, filed on Jan. 31, 2016.

(30) Foreign Application Priority Data

Mar. 12, 2014 (CN) .......................... 2014 1 0089724
Dec. 18, 2015 (CN) .......................... 2015 1 0943772
Aug. 20, 2016 (CN) .......................... 2016 1 0785820

(51) Int. Cl.
*F21V 23/04* (2006.01)
*H04N 5/225* (2006.01)
(Continued)

(52) U.S. Cl.
CPC .......... *F21V 23/0478* (2013.01); *A61B 5/021* (2013.01); *A61B 5/117* (2013.01); *F21K 9/278* (2016.08); *F21V 23/003* (2013.01); *G06F 3/167* (2013.01); *H04N 5/2252* (2013.01); *H04N 5/2256* (2013.01); *H04N 5/2257* (2013.01); *H04N 5/23203* (2013.01);
(Continued)

(58) Field of Classification Search
CPC ............................. Y04S 20/227; Y04S 20/228
See application file for complete search history.

(56) References Cited

U.S. PATENT DOCUMENTS

2008/0221714 A1* 9/2008 Schoettle ............ H04L 12/2829
700/90
2013/0297785 A1* 11/2013 Son ........................ H04L 67/22
709/224
(Continued)

FOREIGN PATENT DOCUMENTS

JP  WO 2014045675 A1 * 3/2014 ............. H05B 6/062

*Primary Examiner* — David N Werner
(74) *Attorney, Agent, or Firm* — Leong C. Lei

(57) ABSTRACT

A smart home-care security device includes a security device that includes a master control board and installed for home use. The master control board is electrically connected with an image-taking module that recognizes a target body, a communication module connectable with multiple electrical appliances, and a detection module, and a reminder module for indicating and reminding. The detection module includes: a microwave measurement module using microwave to detect blood pressure data of the target body; a biological recognition module using microwave to detect a physiological signal of the target body; and a water quality measurement module installed in home water supply facility to inspect and wirelessly transmit water quality. The security device uses the detection module to conduct remote monitoring of the target body in order to establish detailed data of the target body and allow the communication module to provide voice control and wireless connection with the electrical appliances.

14 Claims, 15 Drawing Sheets

(51) Int. Cl.
| | |
|---|---|
| *H04N 5/232* | (2006.01) |
| *H04N 7/18* | (2006.01) |
| *A61B 5/021* | (2006.01) |
| *G06F 3/16* | (2006.01) |
| *A61B 5/117* | (2016.01) |
| *F21V 23/00* | (2015.01) |
| *F21K 9/278* | (2016.01) |
| *G08B 13/196* | (2006.01) |
| *A61B 5/05* | (2006.01) |
| *F21Y 115/10* | (2016.01) |

(52) U.S. Cl.
CPC ............ *H04N 7/183* (2013.01); *A61B 5/0507* (2013.01); *F21Y 2115/10* (2016.08); *G08B 13/19619* (2013.01); *Y04S 20/227* (2013.01); *Y04S 20/228* (2013.01)

(56) References Cited

U.S. PATENT DOCUMENTS

2015/0100245 A1\* 4/2015 Huang ................ A61B 5/0022
                                                                                                             702/19
2016/0291671 A1\* 10/2016 Rider ................ H02J 13/0006

\* cited by examiner

SMART HOME-CARE SECURITY DEVICE

CROSS-REFERENCE TO RELATED APPLICATION

This is a continuation-in-part of U.S. patent application Ser. No. 14/258,029 filed on Apr. 22, 2014 and U.S. patent application Ser. No. 15/011,646 filed on Jan. 31, 2016, both owned by the present applicant.

(a) TECHNICAL FIELD OF THE INVENTION

The present invention relates to a smart home-care security device, which, for each target body in a home environment, provides improved data accuracy through a detection module and allows for connection with all sorts of electrical appliances through a communication module for automatic connection and operation for each target body in the home environment, thereby allowing the security device to expand multiple purposes of application.

(b) DESCRIPTION OF THE PRIOR ART

The progress of modern science and technology makes smart electrical appliances popular in homes. However, different brand products of electrical appliances requires controllers or control manners that are different. In addition, electrical appliances with complicated functionality are hard to operate for children or the elders of a family and mistaken activation of certain functions of the appliances are common.

For modern people, wearable devices are also popular. However, the elder people are generally not accustomed to such wearable devices, and even if they are forced to wear such devices, may remove such devices when not been attended. This causes bad and inaccurate result of monitoring. Thus, although home care devices that require no wearing of such wearable monitoring devices may be available from the market, detection accuracy and detection items are not accurate.

Thus, to improve the accuracy of detection and the items of detection, manufactures conduct manufacture with parts of different materials or analysis of data for the purpose of upgrading the accuracy of the devices provided thereby; this, however, also increases the cost and sale prices. Although functionality and accuracy are enhanced, the operation is nevertheless complicated, not to mention a large and thick operation manual accompanying the sale of such devices. Thus, as a whole, the functionality is excessively complicated and the sale prices are high, making it extremely inconvenient for general users.

A monitoring function, based on the previous description, is commonly used in combination with wireless control that is also commonly known. Products that are available in the market have also be evolved to provide controllability over electrical appliances arranged nearby in the surroundings, to allow a user to conduct a corresponding operation of control to make home living easy and convenient. However, connection with such products of electrical appliances requires wireless devices built in the products, or a remote control be provided, so that such a function may not be applicable to old models of electrical appliances and practical application thereof is still subjected to certain constraint.

SUMMARY OF THE INVENTION

In view of the above, the present invention provides a solution for the problems of insufficiency of detection accuracy, operation range, and connection with surrounding electrical appliances.

To solve the above problem, the present invention provides a smart home-care security device, which comprises: a security device, which is arranged in home lighting for use, the security device being provided therein with a master control board for processing data, the master control board being electrically connected with an image-taking module that is operable to recognize a target body; a communication module, which is arranged in the security device and electrically connected with the master control board, the communication module being connectable with a plurality of electrical appliances; a detection module, which is arranged in the security device and electrically connected with the master control board and comprises: a microwave measurement module, which transmits microwave to the target body to acquire blood pressure data of the target body; a biological recognition module, which transmits microwave to the target body to acquire a physiological signal of the target body; a water quality measurement module, which is adapted to be mounted in home water supply facility for inspecting data of water quality; and a reminder module, which is connectable with the master control board to provide indication and reminder; wherein the security device conducts remote monitoring of the target body by means of the detection module in order to allow the master control board to establish detailed data of the target body acquired by the detection module and to allow the master control board to transmit processing instructions for different target bodies through connection with the communication module.

Preferably, the communication module comprises: an infrared control module, which is arranged in the security device to directly receive the instruction from the master control board for transmission to each of the electrical appliances; a voice recognition module, which is arranged in the security device to receive a voice of the target body for conversion into an instruction transmittable to the master control board and the infrared control module; and a wireless control module, which is arranged in the security device to receive the instruction from the master control board for driving the electrical appliances.

Preferably, the physiological signal of the target body acquired by the biological recognition measurement module comprises one or multiple ones of the following: heartbeat, heart rate, breath, and pulse, which is transmitted to the master control board for processing.

Preferably, the physiological signal of the target body acquired by the microwave measurement module comprises: blood pressure, which is transmitted to the master control board for processing.

Preferably, the image-taking module and the detection module are arranged to selectively increase or decrease the number thereof by at least one or more than one.

Preferably, the reminder module comprises: a target body blood pressure indicator, a target body physiological signal indicator, a water quality indicator, a temperature and humidity indicator, a smoke and gas indicator, an air quality indicator, a target body temperature indicator, and an IP setting indicator, each of the indicators being arranged in the security device and electrically connected with the detection module for being lit on for displaying.

Preferably, the detection module further comprises: a temperature and humidity detection module, a smoke detection module, a gas detection module, an air detection module, and a body temperature detection module, each of the detection modules being arranged in the security device and electrically connected with the master control board to provide a function of corresponding detection, the detection modules being arranged to selectively increase or decrease the number thereof.

Preferably, the security device further comprises: a plurality of LEDs, which is arranged and distributed in the security device to be driven through electrical connection with the master control board.

Preferably, the master control board and the infrared control module are arranged to selectively increase or decrease the number thereof by at least one or more than one.

A smart home-care security device comprises:

a security device, which is provided therein with a master control board for processing data, the master control board being electrically connected with an image-taking module that is operable to recognize a target body; a detection module, which is arranged in the security device and electrically connected with the master control board and comprises: a microwave measurement module, which transmits microwave to the target body to acquire blood pressure data of the target body; a biological recognition module, which transmits microwave to the target body to acquire a physiological signal of the target body; a water quality measurement module, which is adapted to be mounted in home water supply facility for inspecting data of water quality; and a reminder module, which is connectable with the master control board to provide indication and reminder; a communication module, which is arranged in the security device and electrically connected with the master control board, the communication module comprising: an infrared control module, which is arranged in the security device to directly receive the instruction from the master control board for transmission to each of the electrical appliances; a voice recognition module, which is arranged in the security device to receive a voice of the target body for conversion into an instruction transmittable to the master control board and the infrared control module; and a wireless control module, which is arranged in the security device to receive the instruction from the master control board for driving the electrical appliances, wherein the security device conducts remote monitoring of the target body by means of the detection module in order to allow the master control board to establish detailed data of the target body acquired by the detection module and to allow the master control board to transmit processing instructions for different target bodies through connection with the communication module.

Preferably, the detection module further comprises: a temperature and humidity detection module, a smoke detection module, a gas detection module, an air detection module, and a body temperature detection module, each of the detection modules being arranged in the security device and electrically connected with the master control board to provide a function of corresponding detection, the detection modules being arranged to selectively increase or decrease the number thereof.

Preferably, the image-taking module and the detection module are arranged to selectively increase or decrease the number thereof by at least one or more than one.

Preferably, the reminder module comprises: a target body blood pressure indicator, a target body physiological signal indicator, a water quality indicator, a temperature and humidity indicator, a smoke and gas indicator, an air quality indicator, a target body temperature indicator, and an IP setting indicator, each of the indicators being arranged in the security device and electrically connected with the detection module for being lit on for displaying.

Preferably, the master control board and the infrared control module are arranged to selectively increase or decrease the number thereof by at least one or more than one.

The present invention provides a smart home-care security device, which is applicable for use in regular homes and the security device allows for readily installation of modules of different functions at the manufacture side so as to provide flexibility of adjustment in a manufacturing process of a product and also allows for maintenance of integrity of the outside appearance in subsequent function upgrading or enhancing, making it more convenient in practical applications.

Further, the present inventor has proposed previously household detection system that is structured in combination with a lighting device and thus is well aware of the needs of general users through collection of users of products of this kind.

Further, the present invention provides a smart home-care security device, which comprises: a security device, which is provided therein with a master control board for processing data and in electrical connection with an image-taking module that is operable for recognizing a target body and a communication module that is operable for transmission of data and connection with electrical appliances, and is further provided with a detection module, which mainly comprises a microwave measurement module, a biological recognition module, a water quality measurement module, which are arranged in the security device, and a reminder module electrically connected with the master control board so that the security device may use the detection module to conduct remote monitoring of the target body to allow the master control board to establish detailed data of the target body acquired by the detection module and to allow the master control board to transmit different subsequent handling instructions for the target body through connection with the communication module.

Further, the present invention involves new modules that are designed to provide functions of microwave measurement, biological recognition, and water inspection for effectively improving the accuracy of data that is obtained through detection and inspection of the target body so as to be more practical for families that have elder people or children to be taken care of, and comprises a communication module to allow for control of peripheral electrical appliances in connection therewith in an easier way through voice control, without being limited to new or old models of the electrical appliances, so as to make home living smarter and more convenient.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
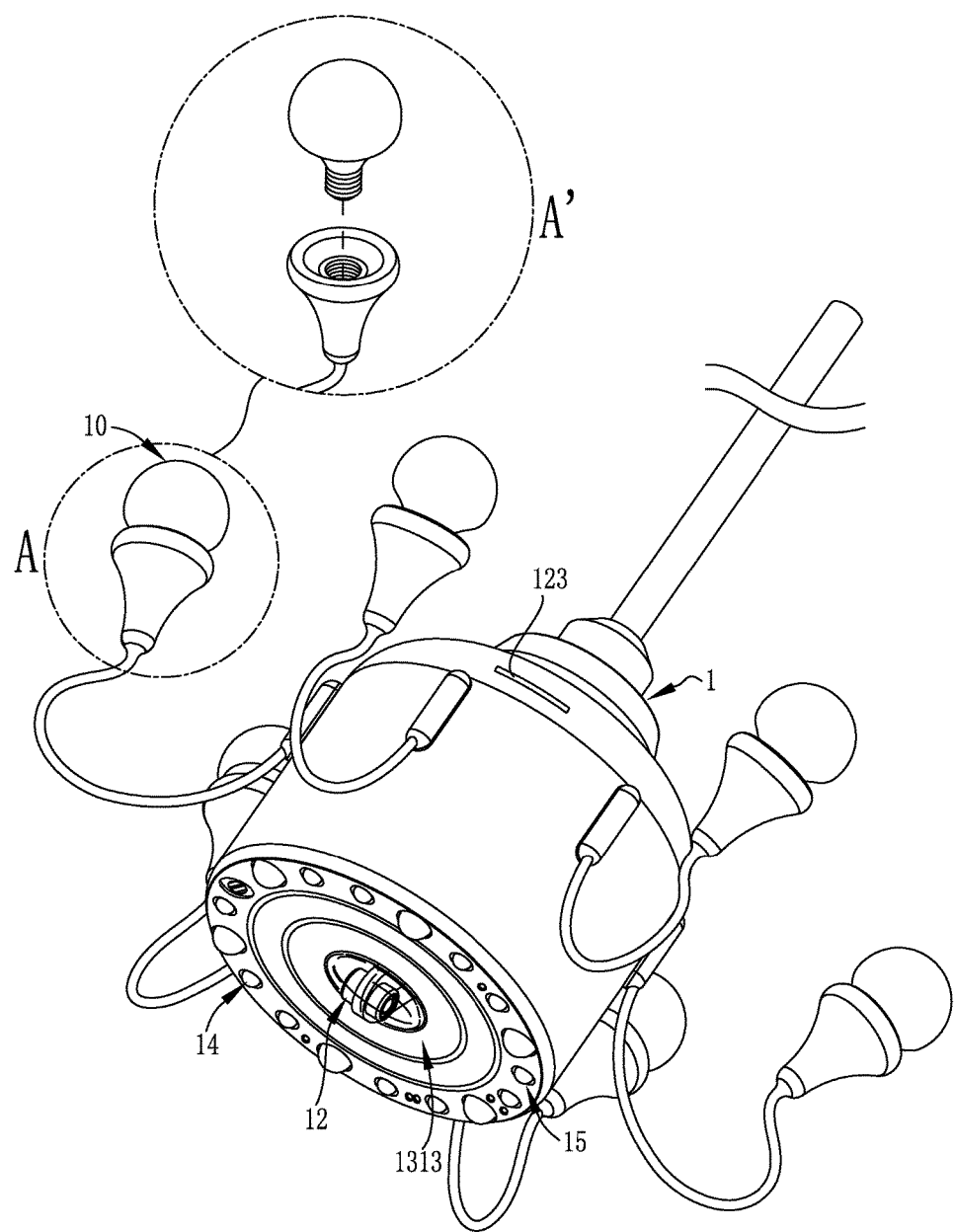
FIG. 1 is a schematic perspective view illustrating the structure of the present invention.

The understanding of the present invention can be enhanced by way of detailed descriptions of the preferred feasible embodiments of the present invention, with reference to the drawings, provided in the following. The present invention provides a smart home-care security device, which, as shown in FIG. 1-4. Part A of FIG. 1 shows an LED 10, which is used in combination with a screw-to-tighten structure commonly seen in regular light bulbs and part A' of FIG. 1 clearly shows the present invention provides a use of being regular home lighting. The LED 10 can be constructed of single warm light, single cold light, or a mixture of warm light and cold light and may receive an adjustment instruction issued from a master control board 11 to blend different color temperatures in order to achieve a function of adjustment to correspond to different scenarios and may also be capable of automatically adjusting light corresponding to the environment by means of the master control board 11, being capable of opening/closing window curtains or being operable through receipt of an input of instruction from external connections, and may store preferences of different users, such as working with a smart phone to change to romantic lighting through mobile application (APP) so as to easily change the entire atmosphere to fit to special holidays or festivals.

Figure 2:
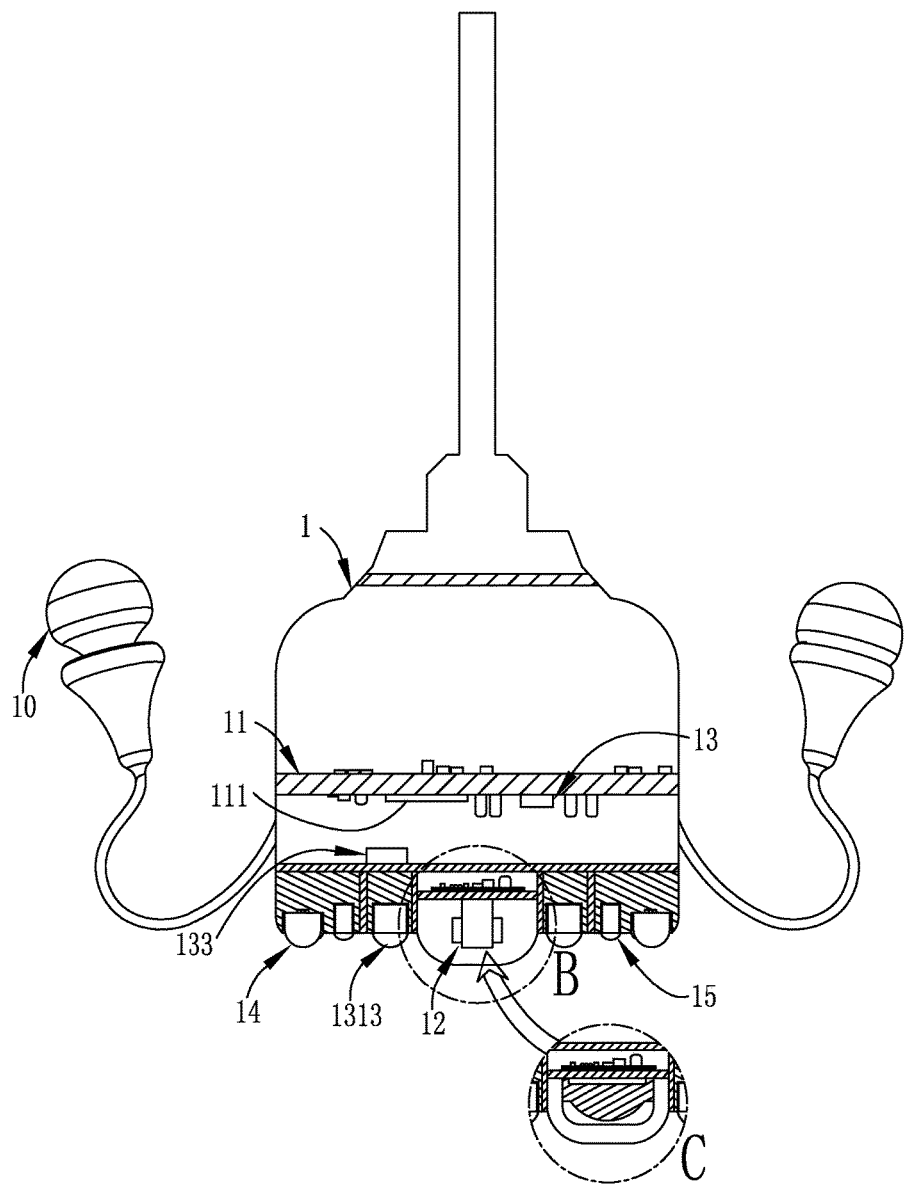
FIG. 2 is a cross-sectional view of the present invention.
Figure 3:
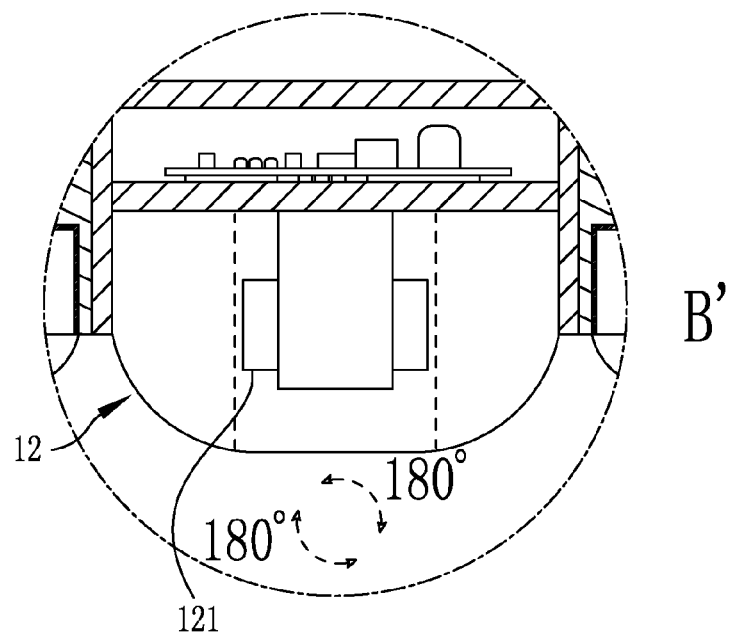
FIG. 3 is a schematic view illustrating an image-taking module shown in circle B' of part B of FIG. 2 according to the present invention.
Figure 4:
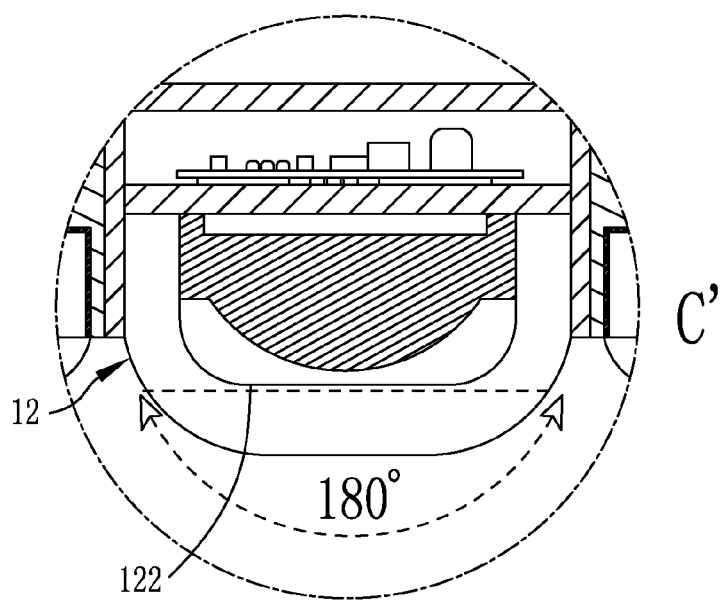
FIG. 4 is a schematic view illustrating an image-taking module shown in circle C' of part C of FIG. 2 according to the present invention.

The security device 1 is provided therein with at least one piece of master control board 11 for operations for processing data acquired by corresponding modules electrically connected therewith, and the master control board 11 is electrically connected with an image-taking module 12 for recognizing an image of a target body 2. The image-taking module 12, as shown in part B of FIG. 2, is generally comprised of at least a dual lens arrangement 121, or may be alternatively constructed by replacing part B with a single fisheye lens 122 shown in part C, such lenses being provided for achieving maximization of surveillance range and ensuring normal operations of corresponding functions; further, the image-taking module 12 is connected with a memory card slot 123 for storage of video image, and as shown in parts B' and C' of FIGS. 3-4, the viewing angle thereof can be greater than or equal to 180° (but not limited to such a fixed angle, for a fisheye lens can be manufactured to provide a viewing angle of 220° according to actual requirement), or alternatively, the dual lens arrangement 121 may be constructed to provide a viewing angle of 360° so as to achieve a purpose of full-view omnidirectional surveillance without any dead zone.

A communication module 13 is arranged in the security device 1 and electrically connected with the master control board 11. The communication module 13 comprises: an infrared control module 131, and is provided therein with a microphone 1311 and a speaker 1312 to receive and broadcast sound effect to achieve a purpose of voice control for further conversion of signal to transmission through the infrared transceiver 1313 to each of electrical appliances 3 to achieve a purpose of control; a voice recognition module 133 to receive voice of the target body 2 for conversion into an instruction transmitted to the master control board 11 and the infrared control module 131; and a wireless control module 132, the wireless control module 132 being communication technology corresponding to WIFI, Bluetooth, Z-WAVE, and ZigBee or other communication technology for connection with a plurality of electrical appliances 3, a handheld smart device (a tablet computer, a smart phone, a handheld or wearable device), a computer (a personal computer, PC), an in-vehicle infotainment system (IVI), and the likes so that remote management or operation of the electrical appliances 3 can be achieved through the communication module 13. In case that the electrical appliances 3 are of old models, it is still possible to achieve connection and operation by means of power extension cord or socket that possesses wireless connection capability, this being commonly known so that no further detail will be needed.

The infrared control module 131, the voice recognition module 133, and the wireless control module 132 can be arranged to provide different combinations to achieve remote control of all sorts of electrical appliances 3, such as:

(1) When the communication module 13 receives an instruction transmitted back thereto from outside the security device 1, the master control board 11 makes a direction transmission to the infrared control module 131 in order to directly control each of the electrical appliances 3 through the infrared transceiver 1313. Or, alternatively, the instruction transmitted from outside the security device 1 is received through the communication module 13, and subjected to conversion into an instruction that is acceptable to the voice recognition module 133 by the master control board 11 through a digital signal processor (DSP) to be subsequently transmitted as an acceptable instruction for the infrared control module 131, subsequent operation being similar to the previous, until control of the electrical appliances 3 is realized.

(2) The microphone 1311 receives voice and the voice is converted by DSP into an instruction acceptable to the voice recognition module 133 to be subsequently transmitted as an acceptable instruction for the infrared control module 131, subsequent operation being similar to the previous, until control of the electrical appliances 3 is realized.

(3) The master control board 11 receives an instruction detected and transmitted from the detection module 14 and transmission is made through the infrared control module 131 to the infrared transceiver 1313 to drive each of the electrical appliances 3. Each of the above applications is not limited to the combination provided above. The main issue is conversion of a received instruction to allow a plurality of infrared transceiver 1313 arranged on the security device 1 to drive all sorts of electrical appliances 3 to achieve an advantage of range expansion and being free of dead zone.

A detection module 14 is arranged in the security device 1 and electrically connected with the master control board 11, and comprises: a microwave measurement module 141, which transmits microwave to the target body 2 to acquire blood pressure data associated with the target body 2; a biological recognition module 142, which transmits microwave to the target body 2 to acquire a physiological signal of the target body 2, the physiological signal comprising one or multiple ones of the following: heartbeat, heart rate, breath, and pulse and the likes; a water quality measurement module 143, which is fixed and installed in home water supply facility (such as: water tower, water reservoir, faucet, and the likes) for use and may inspect, through dissolved oxygen sensor, or other water quality sensors having a similar function, if data of water quality meets regular standards for drinking water, and may also inspect if lead contents, contamination, or number of bacterium exceeds standards. The water quality measurement module 143 can be an externally mounted components or a built-in component, but not limited to any specific type. The microwave the detection module 141 and the biological recognition module 142, which have been mentioned previously, may transmit data back to the master control board 11 to automatically drive corresponding ones of the electrical appliances 3, such as: a television, an air conditioner, a light, or other electrical appliances, may allow for establishing personal dedicated model for a specific user to achieve a purpose of turning on different ones of the electrical appliances 3.

A reminder module 15 comprises: a target body blood pressure indicator 151, a target body physiological signal indicator 152, a water quality indicator 153, a temperature and humidity indicator 154, a smoke and gas indicator 155, an air quality indicator 156, a target body temperature indicator 157, and an IP setting indicator 158, all the above indicators being arranged in the security device 1 and all connected to the master control board 11 to provide reminder or indication through voice or flashing light, except, among them, the IP setting indicator 158 being an indicator light for reminding of proceeding with an operation. The security device 1 may use the detection module 14 to conduct remote monitoring on the target body 2 to allow the master control board 11 establish detailed data of the target body 2 acquired by the detection module 14 and to allow the master control board to transmit an instruction for a subsequent handling operation for the target body 2 through the connection of the communication module 13.

Figure 5:
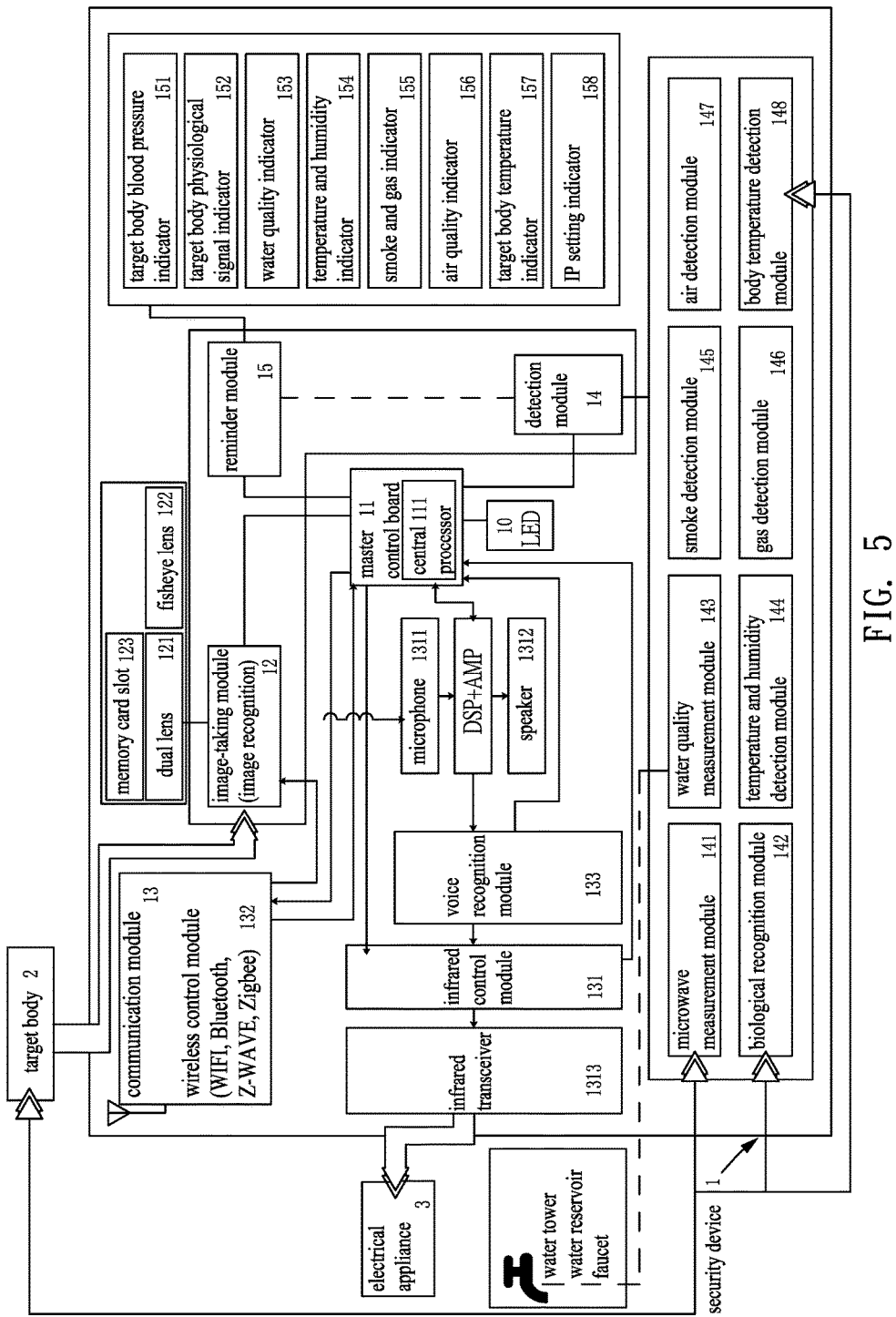
FIG. 5 is a block diagram of the present invention.
Figure 6:
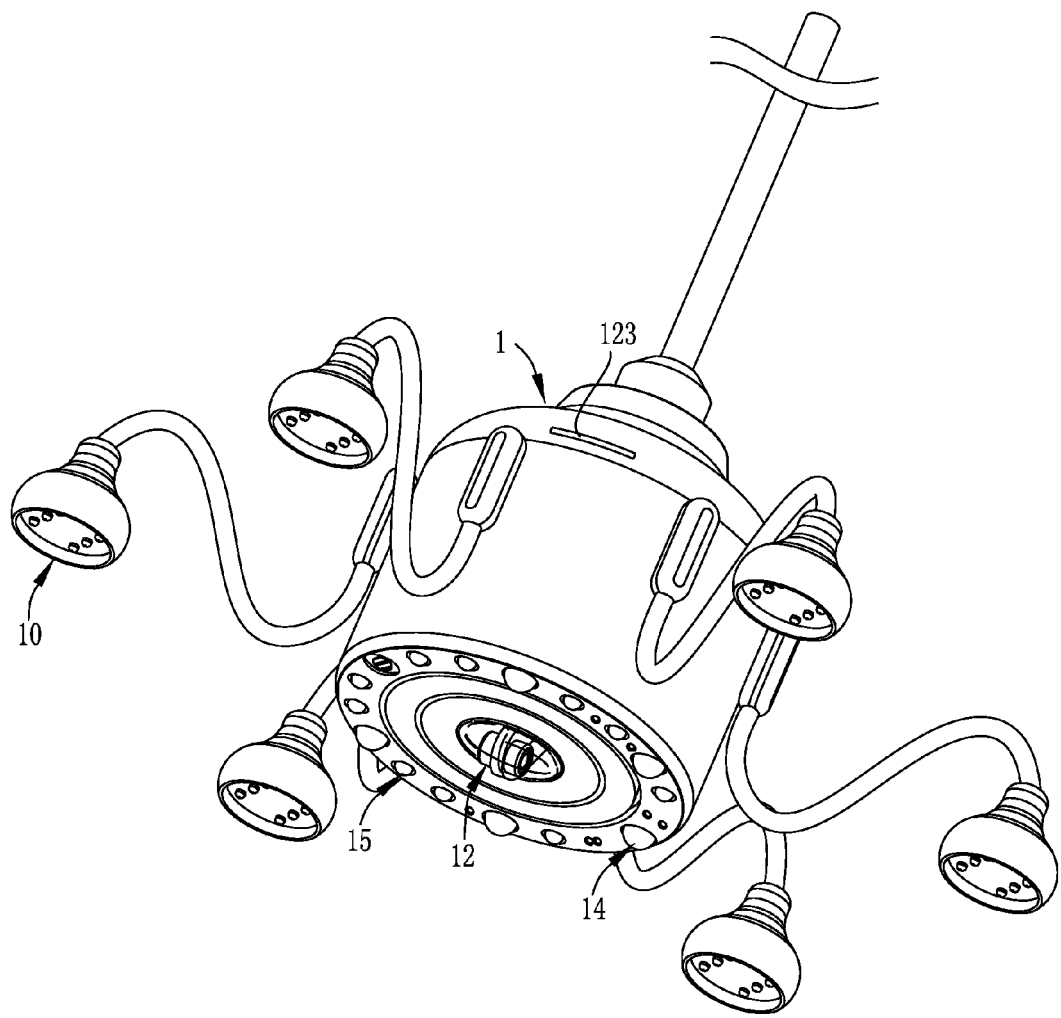
FIG. 6 is a schematic view illustrating a second embodiment of the present invention.
Figure 7:
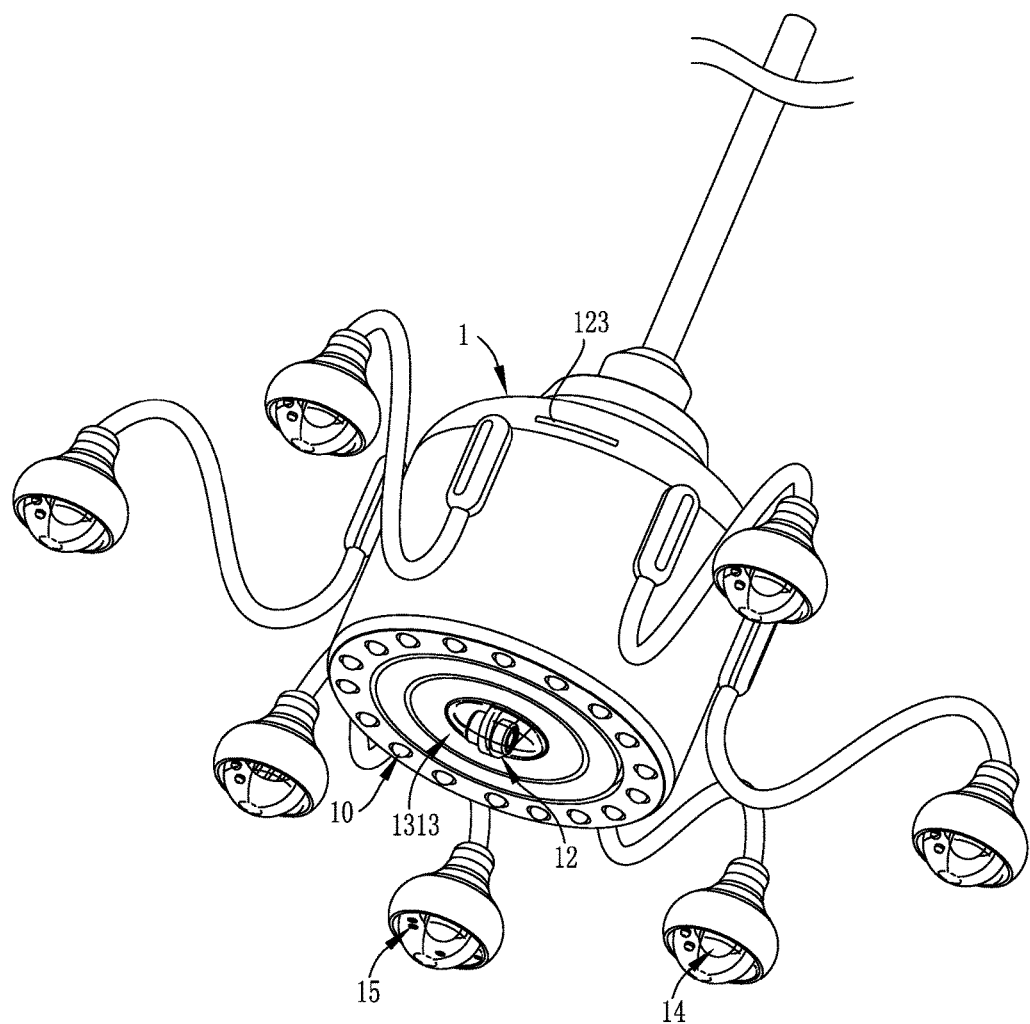
FIG. 7 is a schematic view illustrating a third embodiment of the present invention.
Figure 8:
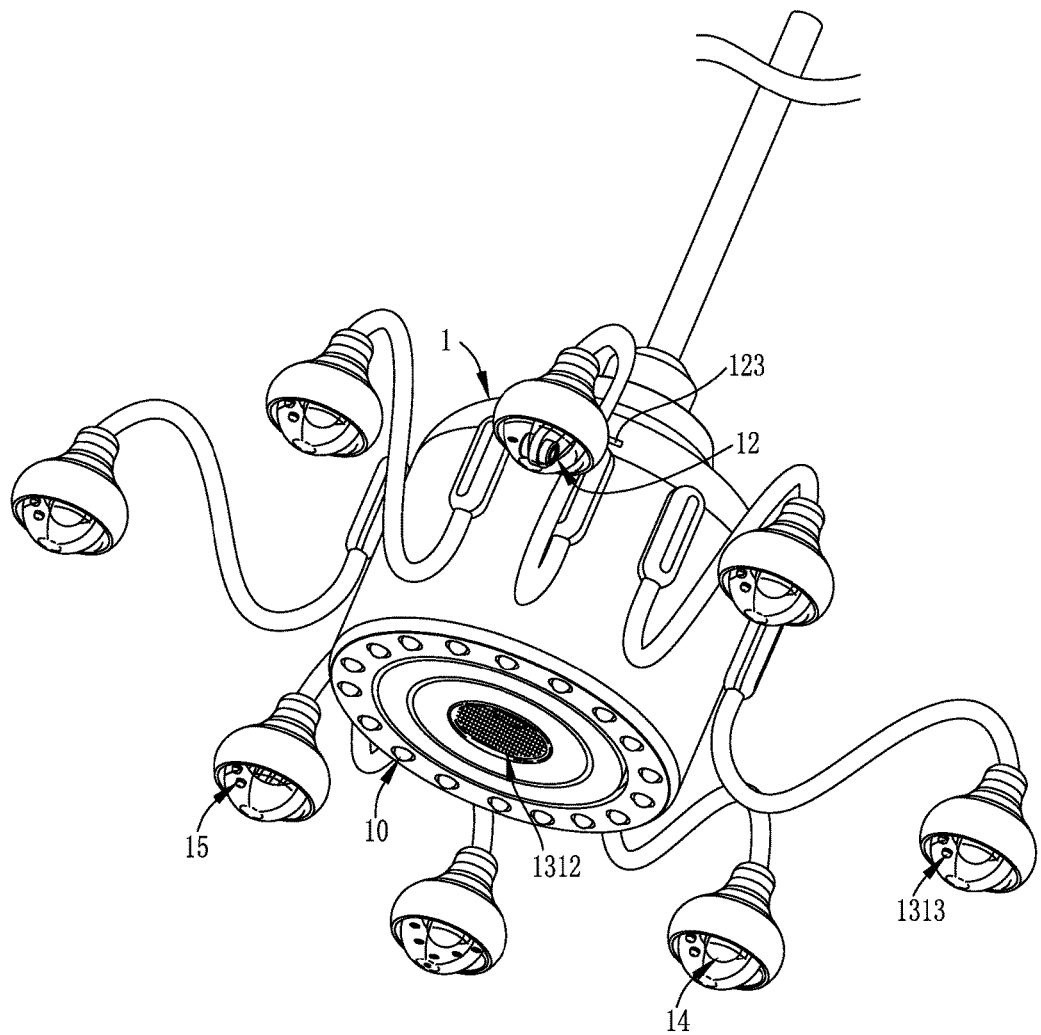
FIG. 8 is a schematic view illustrating a fourth embodiment of the present invention.
Figure 9:
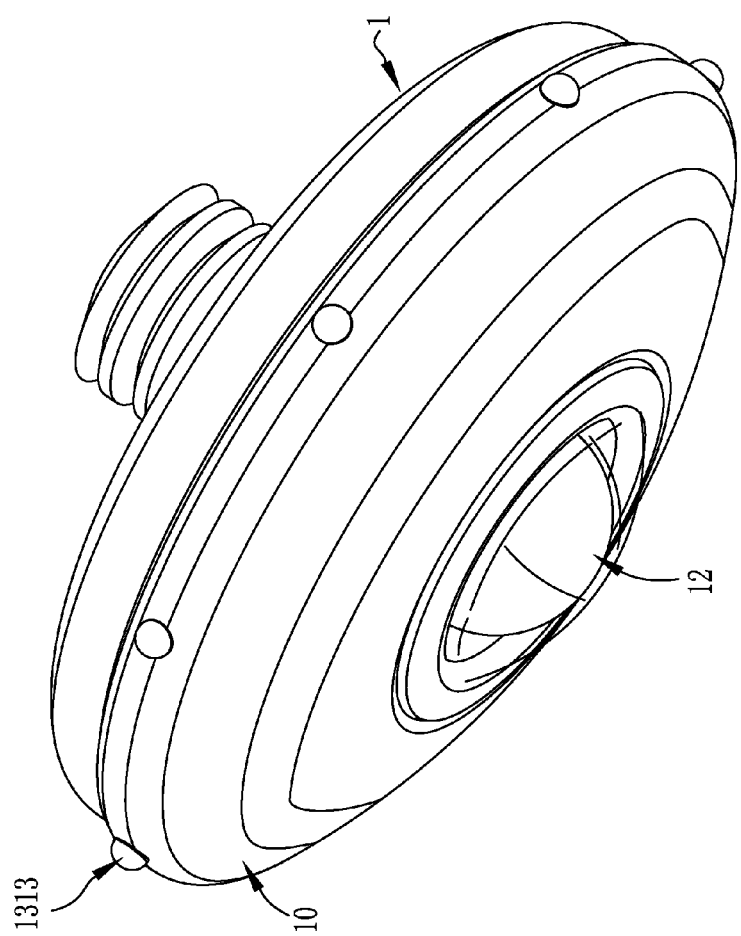
FIG. 9 is a schematic view illustrating a fifth embodiment of the present invention.
Figure 10:
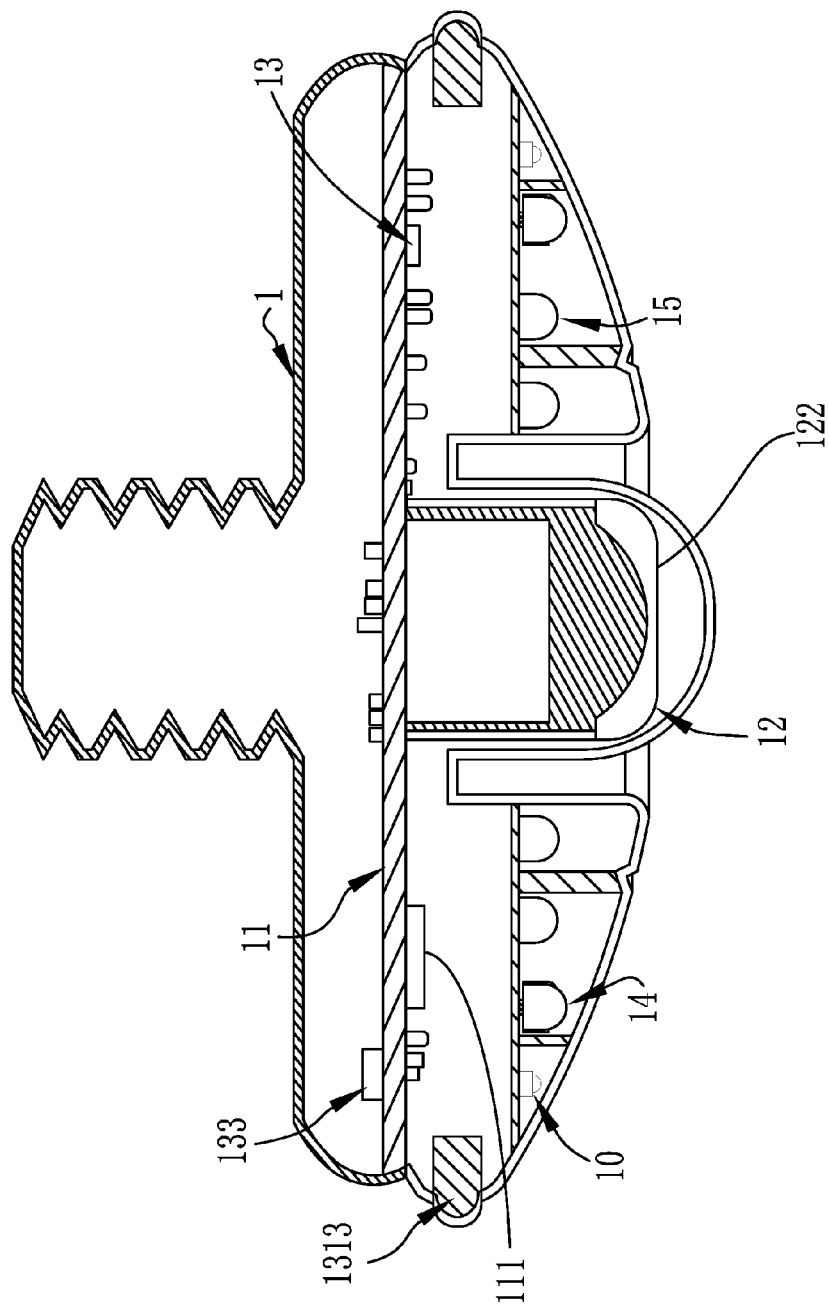
FIG. 10 is a cross-sectional view of the fifth embodiment of the present invention.

Referring to what is shown in FIG. 5, the security device 1 is generally constructed to use a master control board 11 that is provided with a central processor 111 to process data acquired by each module, wherein the target body 2 can be a person (children, adults, or elders) or a pet.

The previously mentioned microwave measurement module 141, specifically speaking, may emit microwave to multiple tracking points of the target body 2 to receive the frequency of pulsation through reflection from the tracking points, wherein the microwave can be micropower impulse radar (MIR), reflected light radiation, radiation pulses, or a combination of any two the three, which can be used in combination with an image of the target body 2 taken by the image-taking module 12 for cross comparison by decomposing the image into video sequence, spatial decomposition, and temporal filtering, so as to use a signal-to-noise ratio generated by the decomposition to determine the blood pressure of the target body 2 thereby acquiring data of high accuracy without direct contact with the target body 2. If the image is individually decomposed for a continuous span of seconds for comparison of a ratio of different between anterior and posterior ones, it is possible to provide precaution to portions where the elders may fall.

The previously mentioned biological recognition module 142, specifically speaking, may be embodied with Doppler radar so that based on a moving signal of a high frequency band of a breath signal, when the breath signal is detected and it is found, based on the moving signal, that the target body 2 is moving in a fixed time, it is determined that the target body 2 is in an abnormal condition, whereby by using standing wave analysis, the detection range can be expanded and abnormality can be detected with high accuracy. Data acquired through the detection can be fed back to the master control board 11 for recoding in Personal Health Record (PHD) so that abnormality, if any, can be transmitted, together with images and the detected data, to a hospital for Smart Medical Home (SMH) and telemedicine, or alternatively, in regular time, remote monitoring of family members, such as children and elders, can be conducted. However, the data that are acquired through frequency of amplitude can only be used to establish data through Bernoulli equation and Doppler radar so that accuracy and applicability are limited. Thus, the present invention uses wave propagation speed corresponding to the frequency of the amplitude and forwarding waves and density of frequency to assist improving the accuracy of data of biological recognition. Further, the biological recognition module 142 is not affected by materials and can be arranged, in a concealed manner, inside the security device 1 to make the outside appearance beautiful. However, the way of use of the biological recognition module 142 is not limited to one of these and at least two ways can be used in combination through the above measures of data acquisition.

As to the previously mentioned water quality measurement module 143, specifically speaking, for total dissolved solids (TDS), general oxygen dissolved in water, the dissolution rate is determined by temperature, total pressure of water surface, and the total amount of solids dissolved in water, where the higher the atmospheric pressure is, the greater the capability of dissolution in water will be, materials that are commonly used including: an electrode made of gold or platinum, in combination with a counter-electrode made of silver with a membrane covering therebetween to separate electrolyte and measured liquid so as to protect dissolved oxygen sensor and prevent escape of electrolyte and also to prevent invasion of external materials, wherein through an electrical voltage applied between the electrode and the counter-electrode, based on ratio between electron and oxygen molecules, the safety of water quality can be monitored, of which the result can be transmitted through the wireless control module 132 to the master control board 11 to achieve a purpose of water quality monitoring. A filter or a device that provides a similar function can be additionally provided for assistance to make water quality even much safer. Such a measurement solution can also be monitored by means of electrical conductivity (EC).

Regarding to the previously mentioned microwave measurement module 141 and the biological recognition module 142, if it is determined that the target body 2 is in a normal rest condition, the master control board 11 may temporarily cut off video recording acquired through the image-taking module 12, while the detection operation is kept on progress, in order to eliminate the concern of leakage of user's privacy. When the target body 2 under detection exhibits abnormality, the image-taking module 12 is re-started to take image (such as photographing or video recoding) for transmission to emergency contact persons, attendants, or hospital or emergency rescue facility in default setting in the system so that addition or removal can be made by a user according to practical need and no upper limit is provided for the contact parties. For all data of the user's body detected as described above, in an event of intelligence deterioration, it is still recommended that a wearable device be used as an assistive measure that may be in connection with the communication module 13 to achieve a purpose of watching and tracking the location thereof.

However, in addition to the previously discussed microwave measurement module 141, biological recognition module 142, and water quality measurement module 143, the detection module 14 further comprises: a temperature and humidity detection module 144, which detects an environment temperature and humidity for transmission to the master control board 11 and issues an instruction in a normal condition to drive the temperature and humidity indicator 154 to light on for displaying, such as when the humidity exceeds a predetermined threshold, a corresponding one of electrical appliances 3 being activated to conduct dehumidification; a smoke detection module 145, which detects environment smoke so that when the detection exceeds a threshold, corresponding data will be transmitted to a wireless device through the wireless control module 132 of the communication module 13 to issue a broadcast alarm through the speaker 1312 and AMP and also driving the smoke and gas indicator 155 to light on or to flash for displaying, wherein if the detected environment reaches the most dangerous level, then corresponding detection data and images will be transmitted to a fire department for subsequent handling; a gas detection module 146, which is generally operable to detect a harmful gas outside the security device 1 and to provide a reminder through connection with a smoke and gas indicator 155; an air detection module 147, which is generally operable to detect and monitor suspended particles in air and to display the current quality with different colors through connection with an air quality indicator 156, wherein blue displaying indicates a normal condition, yellow indicating a middle level, while red displaying indicate the poorest condition, and connection can be made, according to air qualities, with corresponding ones of the electrical appliances 3, such as setting an air purification device into operation; a body temperature detection module 148, which is generally operable to detect a body temperature of a family member and, through connection with a target body temperature indicator 157, to display blue in a normal condition and to issue an alarm through the communication module 13 when the detection is higher than a threshold. For the detection module 14 discussed above, when abnormality is detected, the system will, as a default setting, make an immediate transmission to a handheld device of a user to display detailed on-site data so as to provide complete monitoring of the home environment.

Figure 11:
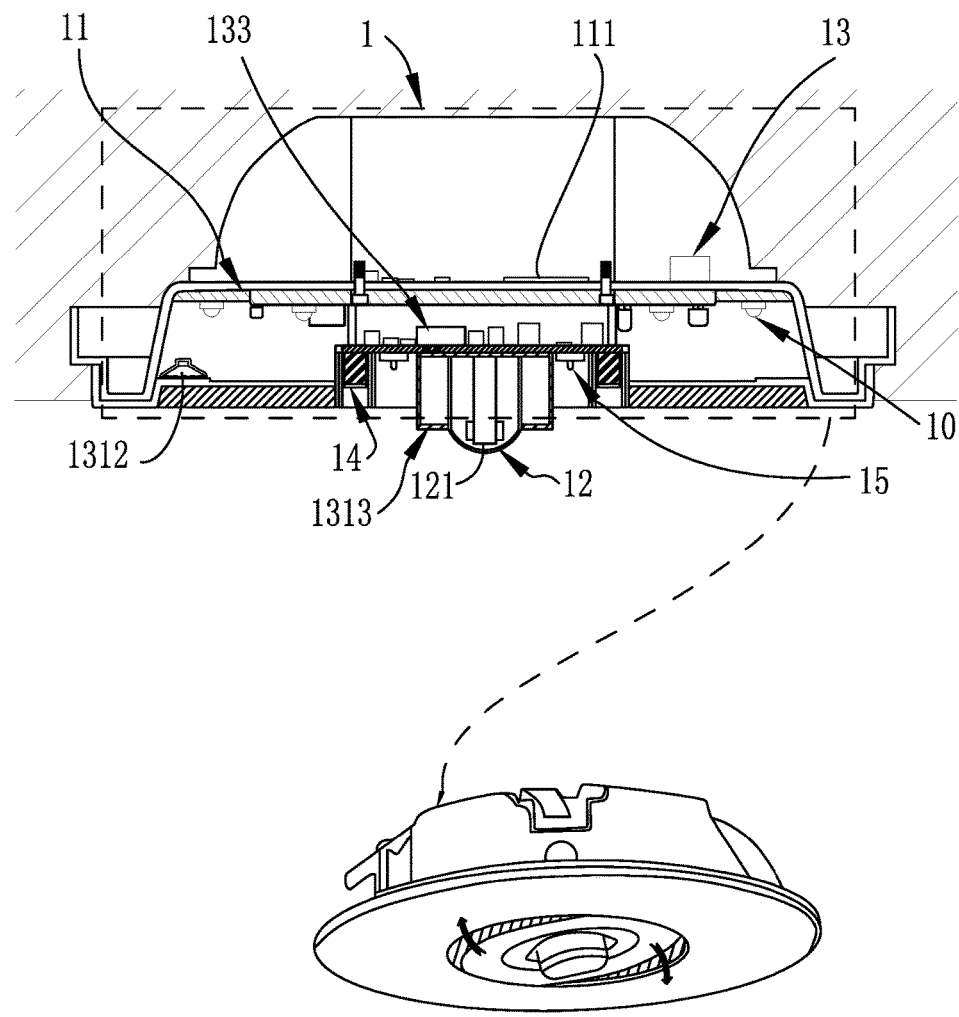
FIG. 11 is a schematic view illustrating a sixth embodiment of the present invention.
Figure 12:
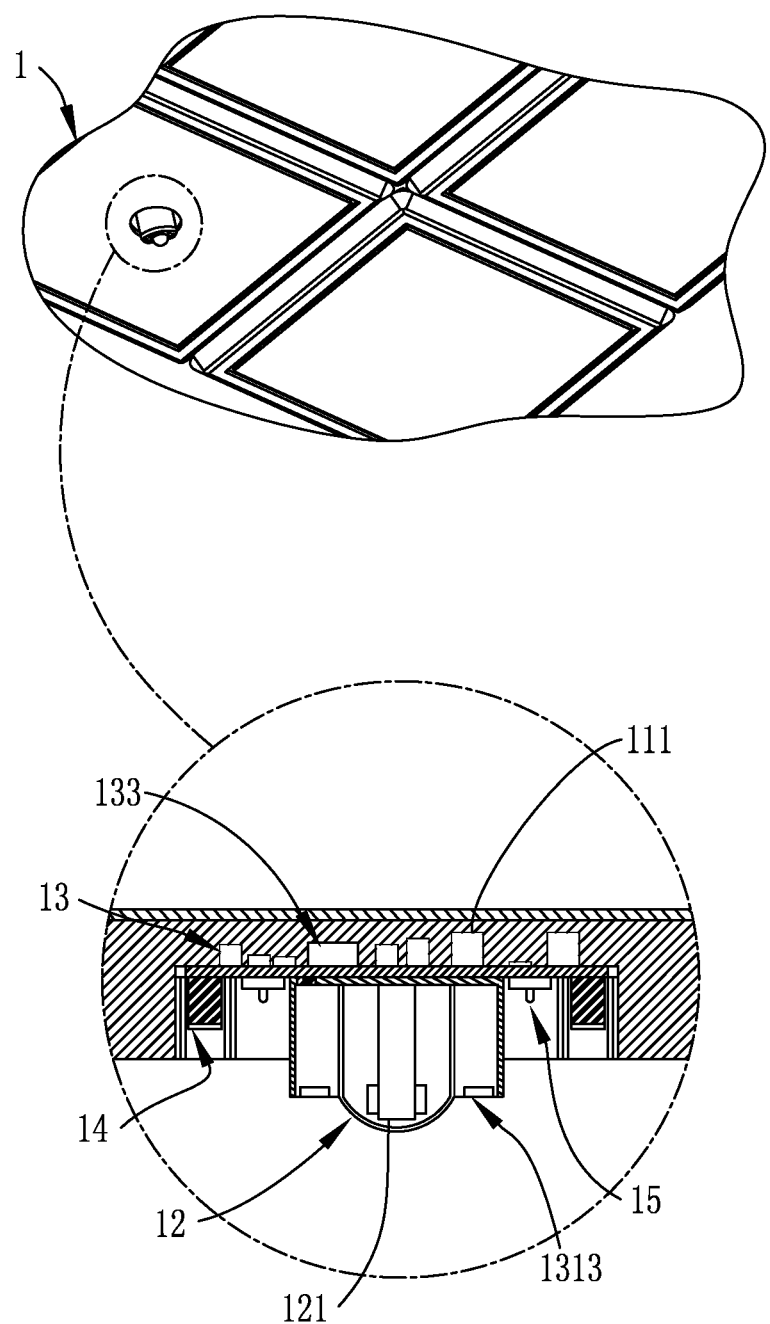
FIG. 12 is a schematic view illustrating a seventh embodiment of the present invention.
Figure 13:
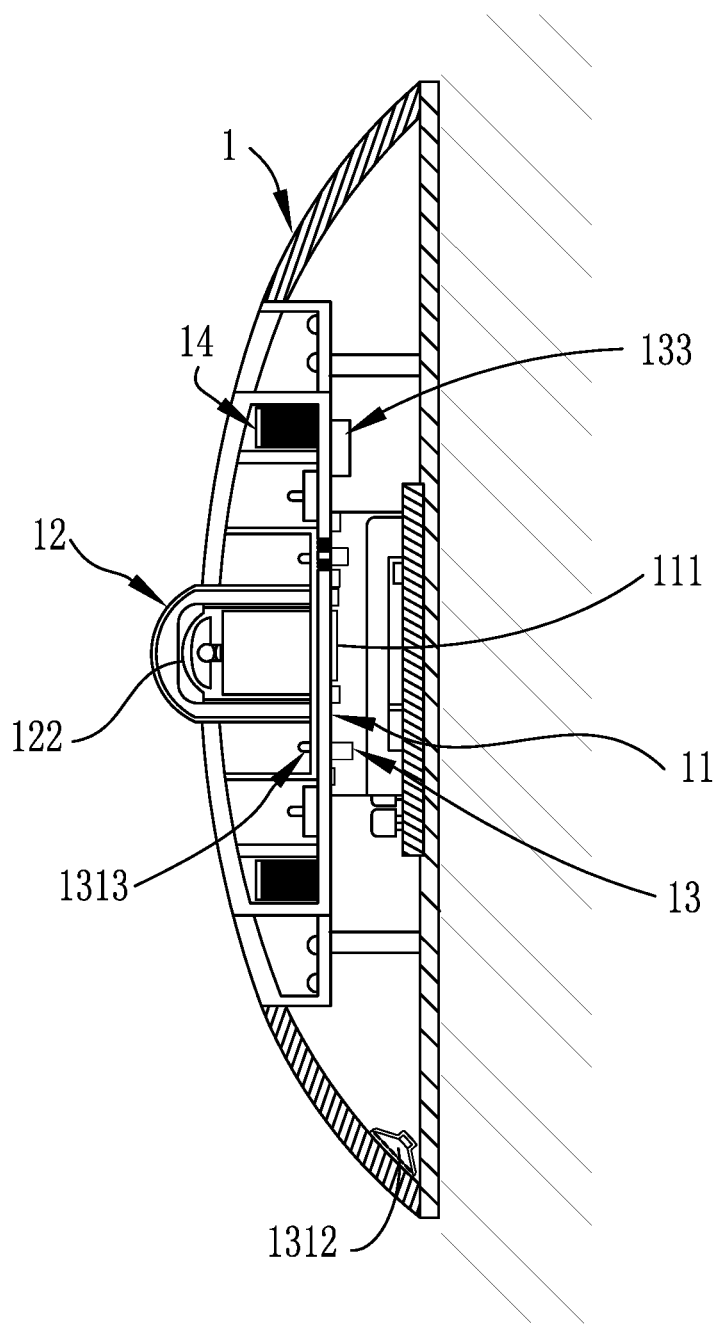
FIG. 13 is a schematic view illustrating an eighth embodiment of the present invention.

Referring to FIGS. 6-13, second to eighth embodiments of the present invention are illustrated, of which the structures are simple modifications of the first embodiment that has been discussed previously, and are generally formed by changing the arrangement locations of the image-taking module 12, the detection module 14, the reminder module 15, and the LED 10, and each module, but achieving the same purpose and function as those illustrated with a block diagram of FIG. 5, the change and adjustment being made for mounting and installation in different types of lighting fixture, such as those illustrated in FIGS. 11-13, which are, in sequence, an embedded light, a fluorescent panel, and a wall lamp, making the range of application wider and not limited, details of the structure being omitted herein. Further, due to they still possessing a function of lighting, since heat, even minor, may be generated by the LED 10 in lighting, an insulation wall is provided between LED 10 and the detection module 14 to ensure normal operation of the detection module 14.

Figure 14:
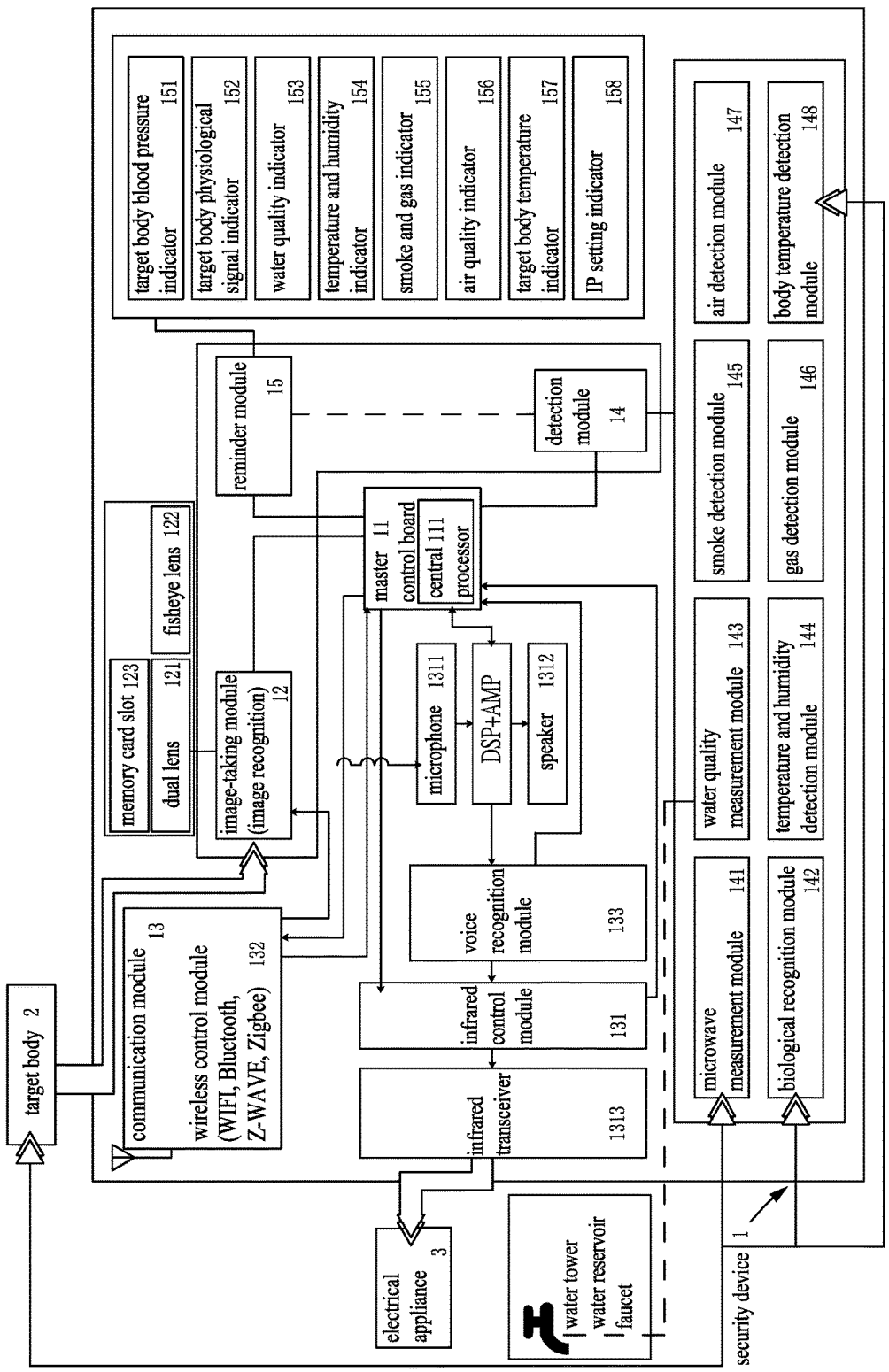
FIG. 14 is a block diagram of a ninth embodiment of the present invention.
Figure 15:
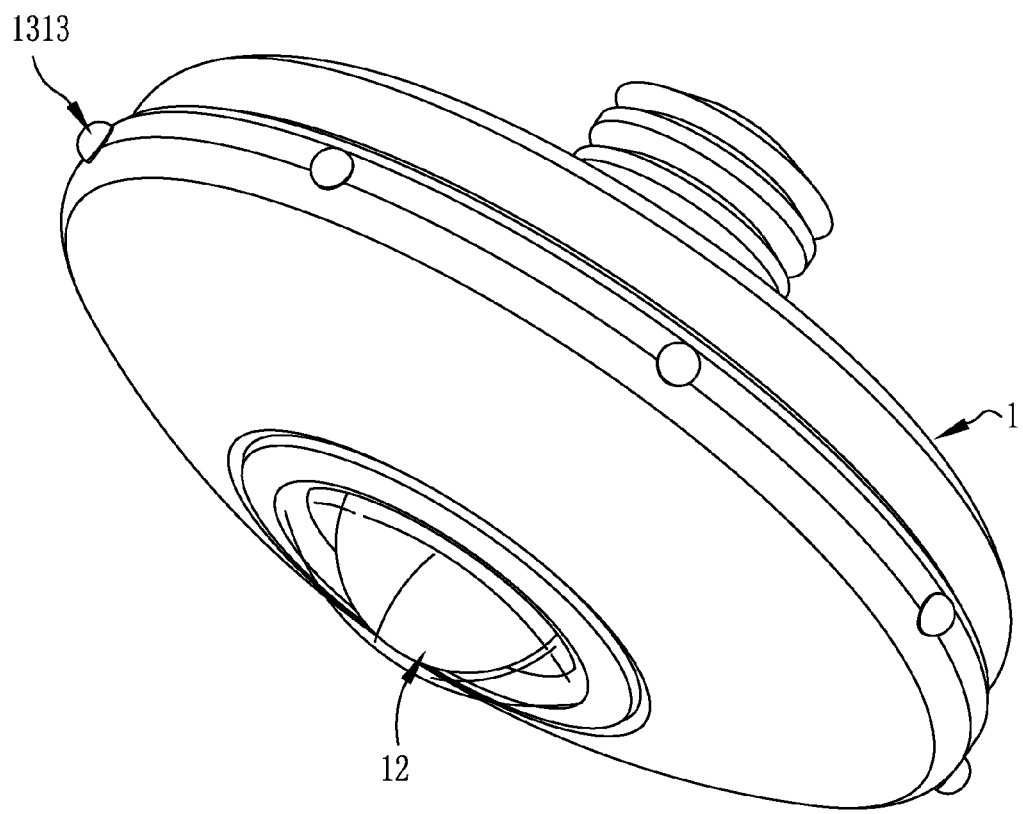
FIG. 15 is a perspective view of the ninth embodiment of the present invention.
Figure 16:
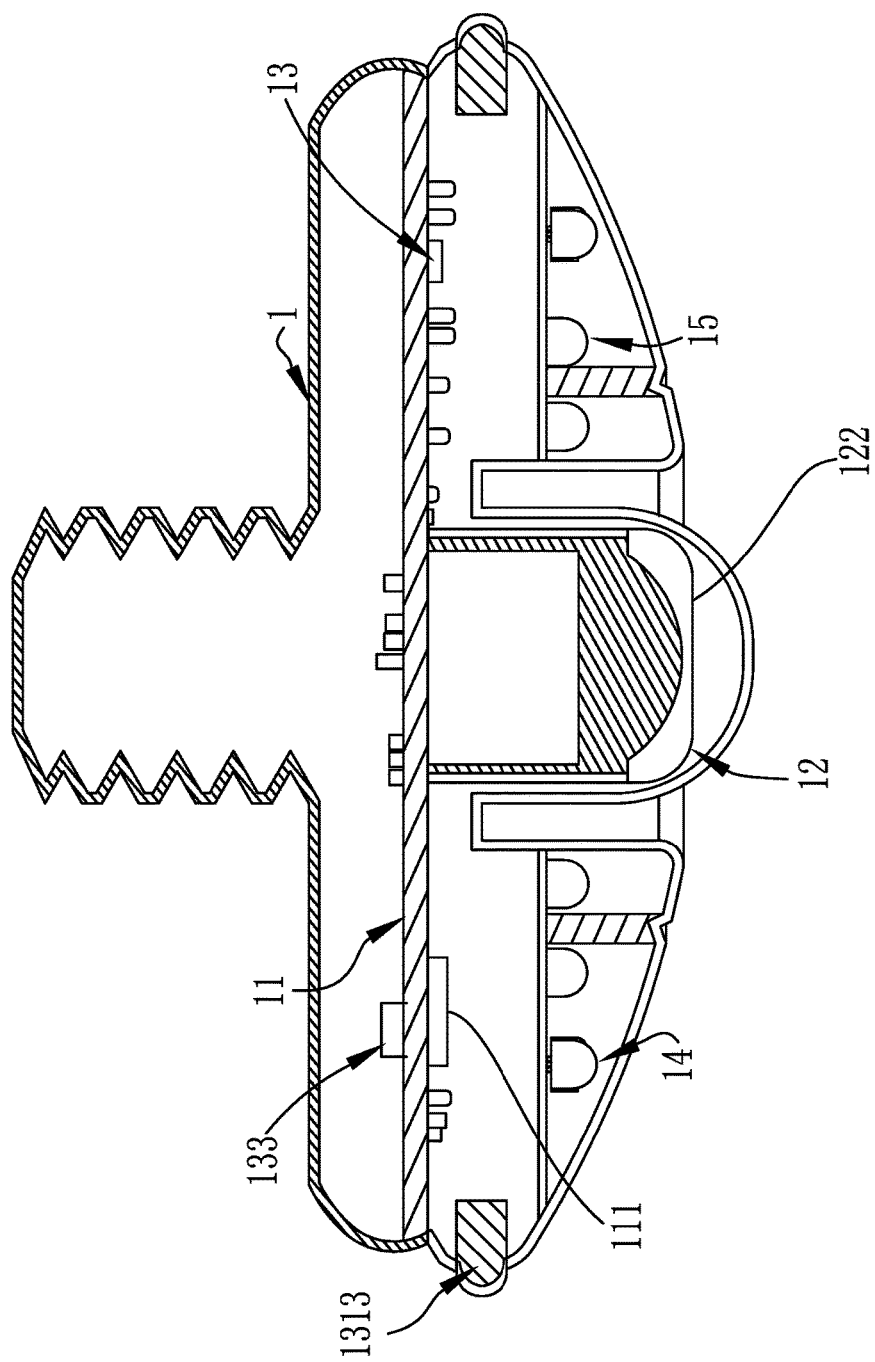
FIG. 16 is a cross-sectional view of the ninth embodiment of the present invention.

Further referring to FIGS. 14-16, a ninth embodiment of the present invention is shown, which comprises: a security device 1, which is provided, in an interior thereof, with a master control board 11 for processing data, the master control board 11 being electrically connected with an image-taking module 12 for recognizing a target body 2, and is also provided with a detection module 14 arranged in the security device 1, wherein the detection module 14 comprises: a microwave measurement module 141, which emits microwave to measure the blood pressure of the target body 2; a biological recognition module 142, which transmits microwave to the target body 2 to acquire a corresponding physiological signal (such as data including heartbeat, heart rate, breath, and pulse); and a water quality measurement module 143, which is fixed and installed in home water supply facility for operation and may inspect, through installation of dissolved oxygen sensor, or other water quality sensors having a similar function, if data of water quality meets regular standards for drinking water, and may also inspect if lead contents, contamination, or number of bacterium exceeds standards; and is also provided with a reminder module 15, which, as shown in a block diagram of FIG. 11, comprises a plurality of indicators respectively corresponding to different ones of the detection modules 14 to carry out corresponding indication and reminding; a communication module 13, which comprises an infrared control module 131 and a wireless control module 132, the two modules being operable to convert an orally issued instruction from the target body 2, through a microphone 1311, a digital signal processor (DSP), and infrared transceivers 1313, into an instruction corresponding to the security device 1 to allow a plurality of infrared transceivers 1313 arranged on the security device 1 to drive corresponding ones of surrounding electrical appliances 3 in a manner of being free of dead zone.

It can be seen from the above-described ninth embodiment that the security device 1 is not provided with an LED 10 for lighting purpose, meaning the security device 1 can be designed and structured as a home decoration article, to reduce the perception of existence thereof and also allowing for dead-zone-free surveillance and voice control of the surrounding electrical appliances, making home living easy and convenient.

The present invention provides a smart home-care security device, which is provided therein with a master control board 1 and an infrared control module 131 that can be separate or combined in a manner of being one piece or more than one piece for use according to the manufacturing specification and models thereof. The seven (7) modules involved in the detection module 14 can be arranged to increase or decrease the number thereof during manufacture, and are not limited to any specific types.

In summary, the present invention provides a smart home-care security device, which comprises, installed therein, multiple detection modules 14 to improve, by a great extent, accuracy of detection and comprises a master control board 1 to data of each target body 2, allowing a communication module 13 to easily accommodate electrical appliances originating from different countries and of different brands so as to establish a series of linked operations, through unified processing with an internal central processor 111, to achieve monitoring of personal security of each family member. Further, the present invention is more economically beneficial than other products of the kind and does not require additional wearable detection devices, while still carrying out detection of high accuracy, and providing data specifically dedicated to each person, providing rich applicability of smart home. It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:

1. A smart home-care security device, adapted to use with home lighting, comprising:
    a security device, which is arranged in home lighting for use, the security device being provided therein with a master control board for processing data, the master control board being electrically connected with an image taking module that is operable to recognize a target body;
    a communication module, which is arranged in the security device and electrically connected with the master control board, the communication module being connectable with a plurality of electrical appliances;
    a detection module, which is arranged in the security device and electrically connected with the master control board and comprises:
        a microwave measurement module, which transmits microwave to the target body to acquire blood pressure data of the target body;
        a biological recognition module, which transmits microwave to the target body to acquire a physiological signal of the target body;
        a water quality measurement module, which is adapted to be mounted in home water supply facility for inspecting data of water quality; and
    a reminder module, which is connectable with the master control board to provide indication and reminder;
    wherein the security device conducts remote monitoring of the target body by means of the detection module in order to allow the master control board to establish detailed data of the target body acquired by the detection module and to allow the master control board to transmit processing instructions for different target bodies through connection with the communication module.

2. The smart home-care security device according to claim 1, wherein the communication module comprises:
    an infrared control module, which is arranged in the security device to directly receive the instruction from the master control board for transmission to each of the electrical appliances;
    a voice recognition module, which is arranged in the security device to receive a voice of the target body for conversion into an instruction transmittable to the master control board and the infrared control module; and
    a wireless control module, which is arranged in the security device to receive the instruction from the master control board for driving the electrical appliances.

3. The smart home-care security device according to claim 1, wherein the physiological signal of the target body acquired by the biological recognition measurement module comprises one or multiple ones of the following: heartbeat, heart rate, breath, and pulse, which is transmitted to the master control board for processing.

4. The smart home-care security device according to claim 1, wherein the physiological signal of the target body acquired by the microwave measurement module comprises: blood pressure, which is transmitted to the master control board for processing.

5. The smart home-care security device according to claim 1, wherein the image-taking module and the detection module are arranged to selectively increase or decrease the number thereof by at least one or more than one.

6. The smart home-care security device according to claim 1, wherein the reminder module comprises: a target body blood pressure indicator, a target body physiological signal indicator, a water quality indicator, a temperature and humidity indicator, a smoke and gas indicator, an air quality indicator, a target body temperature indicator, and an IP setting indicator, each of the indicators being arranged in the security device and electrically connected with the detection module for being lit on for displaying.

7. The smart home-care security device according to claim 1, wherein the detection module further comprises: a temperature and humidity detection module, a smoke detection module, a gas detection module, an air detection module, and a body temperature detection module, each of the detection modules being arranged in the security device and electrically connected with the master control board to provide a function of corresponding detection, the detection modules being arranged to selectively increase or decrease the number thereof.

8. The smart home-care security device according to claim 1, wherein the security device further comprises: a plurality of LEDs, which is arranged and distributed in the security device to be driven through electrical connection with the master control board.

9. The smart home-care security device according to claim 2, wherein the master control board and the infrared control module are arranged to selectively increase or decrease the number thereof by at least one or more than one.

10. A smart home-care security device, comprising:
    a security device, which is provided therein with a master control board for processing data, the master control board being electrically connected with an image-taking module that is operable to recognize a target body;

a detection module, which is arranged in the security device and electrically connected with the master control board and comprises:
- a microwave measurement module, which transmits microwave to the target body to acquire blood pressure data of the target body;
- a biological recognition module, which transmits microwave to the target body to acquire a physiological signal of the target body;
- a water quality measurement module, which is adapted to be mounted in home water supply facility for inspecting data of water quality;
- and a reminder module, which is connectable with the master control board to provide indication and reminder;

a communication module, which is arranged in the security device and electrically connected with the master control board, the communication module comprising:
- an infrared control module, which is arranged in the security device to receive directly the instruction from the master control board for transmission to each of the electrical appliances;
- a voice recognition module, which is arranged in the security device to receive a voice of the target body for conversion into an instruction transmittable to the master control board and the infrared control module; and a wireless control module, which is arranged in the security device to receive the instruction from the master control board for driving the electrical appliances, wherein the security device conducts remote monitoring of the target body by means of the detection module in order to allow the master control board to establish detailed data of the target body acquired by the detection module and to allow the master control board to transmit processing instructions for different target bodies through connection with the communication module.

11. The smart home-care security device according to claim 10, wherein the detection module further comprises: a temperature and humidity detection module, a smoke detection module, a gas detection module, an air detection module, and a body temperature detection module, each of the detection modules being arranged in the security device and electrically connected with the master control board to provide a function of corresponding detection, the detection modules being arranged to selectively increase or decrease the number thereof.

12. The smart home-care security device according to claim 10, wherein the image-taking module and the detection module are arranged to selectively increase or decrease the number thereof by at least one or more than one.

13. The smart home-care security device according to claim 10, wherein the reminder module comprises: a target body blood pressure indicator, a target body physiological signal indicator, a water quality indicator, a temperature and humidity indicator, a smoke and gas indicator, an air quality indicator, a target body temperature indicator, and an IP setting indicator, each of the indicators being arranged in the security device and electrically connected with the detection module for being lit on for displaying.

14. The smart home-care security device according to claim 10, wherein the master control board and the infrared control module are arranged to selectively increase or decrease the number thereof by at least one or more than one.

* * * * *